United States Patent [19]

Jasys

[11] 4,381,263
[45] Apr. 26, 1983

[54] PROCESS FOR THE PREPARATION OF PENICILLANIC ACID ESTERS

[75] Inventor: Vytautas J. Jasys, New London, Conn.

[73] Assignee: Pfizer Inc., New York, N.Y.

[21] Appl. No.: 341,081

[22] Filed: Jan. 25, 1982

Related U.S. Application Data

[63] Continuation-in-part of Ser. No. 246,482, Mar. 23, 1981, abandoned.

[51] Int. Cl.³ ............................................. C07D 499/08
[52] U.S. Cl. ........................... 260/239.1; 260/245.2 R; 424/271
[58] Field of Search ...................... 260/239.1, 245.2 R

[56] References Cited

U.S. PATENT DOCUMENTS 4,234,579 11/1980 Barth .................................. 424/246
4,244,951 1/1981 Bigham .............................. 424/250

FOREIGN PATENT DOCUMENTS 881675 8/1980 Belgium .
2044255 10/1980 United Kingdom .

Primary Examiner—Glennon H. Hollrah
Assistant Examiner—Vera C. Clarke
Attorney, Agent, or Firm—Charles J. Knuth; Albert E. Frost; James M. McManus

[57] ABSTRACT

A process for the preparation of chloromethyl esters of penicillanic acids, using iodochloromethane or bromochloromethane and a tetraalkylammonium salt of the penicillanic acid, and their use in processes for the synthesis of penicillanic acid esters, using a halomethyl ester and the tetraalkylammonium salt of the penicillanic acid, which readily hydrolyze in vivo to antibacterial penicillins and the beta-lactamase inhibitor penicillanic acid sulfone.

20 Claims, No Drawings

PROCESS FOR THE PREPARATION OF PENICILLANIC ACID ESTERS

CROSS REFERENCE TO RELATED APPLICATION

This application is a continuation-in-part of application Ser. No. 246,482, filed Mar. 23, 1981, now abandoned.

BACKGROUND OF THE INVENTION

Despite the wide use and acceptance of penicillins and cephalosporins, beta-lactam antibiotics, in combating bacterial infections, there are certain members within the group that are not active against resistant microorganisms because of the organism's ability to produce a beta-lactamase enzyme which reacts with beta-lactam antibiotic to produce products devoid of antibacterial activity. However, certain substances have the ability to inhibit beta-lactamases, and when used in combination with a penicillin or cephalosporin can increase or enhance the antibacterial effectiveness of the antibiotic against certain beta-lactamase producing microorganisms.

West German Offenlegungsschrift No. 2,824,535 published Dec. 14, 1978 teaches that penicillanic acid sulfone is such an effective beta-lactamase inhibitor. In addition, it is taught in said application that certain esters of penicillanic acid sulfone are readily hydrolyzable in vivo giving high blood levels of this beta-lactamase inhibitor. Further, U.K. patent application No. 2,044,255 and U.S. Pat. No. 4,244,951 also teaches that halomethyl esters of penicillanic acid sulfone can be coupled through the carboxy group of an antibacterial penicillin to give compounds with readily hydrolyzable esters which degrade in vivo into anti-bacterial penicillins and the beta-lactamase inhibitor penicillanic acid sulfone.

U.K. patent application No. 2,044,255 further teaches that the intermediate chloromethyl penicillanate sulfone can be prepared by coupling the potassium salt of penicillanic acid sulfone with chloroiodomethane in the presence of a catalytic amount of tetrabutylammonium sulfate. In addition it is reported that the tetrabutylammonium salts of certain penicillanic antibacterial agents can be coupled with alpha-haloalkyl penicillanate sulfones to give compounds with readily hydrolyzable esters which degrade in vivo into antibacterial penicillins and penicillanic acid sulfone.

SUMMARY OF THE INVENTION

The first process of the present invention is for the preparation of a compound of the formula

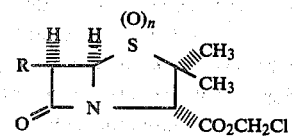

wherein n is an integer of 0 or 2, R is
(a) hydrogen

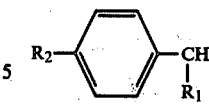

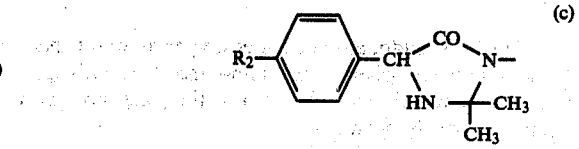

wherein $R_2$ is hydrogen or hydroxy and $R_1$ is azido, amino, 1-methoxycarbonylpropen-2-ylamino or carbobenzyloxyamino, which comprises contacting one mole of a compound of the formula

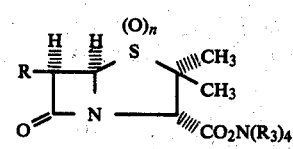

wherein $R_3$ is alkyl of one to four carbon atoms, with at least one mole of iodochloromethane or bromochloromethane at from about $-20°$ C. to about 25° C. with the proviso that when n is 2, R is hydrogen.

A preferred feature of the claimed process is the use of excess bromochloromethane.

An especially preferred feature of the claimed process is the preparation of those compounds where R is hydrogen, $R_3$ is n-butyl and n is 2, and where R is

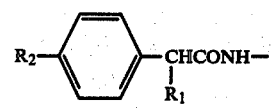

where $R_2$ is hydrogen, n is 0, $R_3$ is n-butyl and $R_1$ is azido, amino or 1-methoxycarbonylpropen-2-ylamino.

The products of this process invention are useful intermediates in preparing compounds with readily hydrolyzable esters which degrade in vivo into beta-lactam antibiotics and the beta-lactamase inhibitor penicillanic acid sulfone.

A second process of the present invention is for the preparation of compounds of the formula

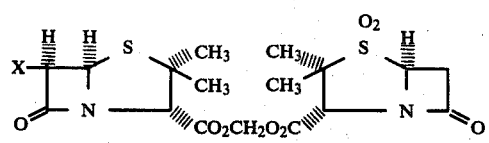

wherein X is

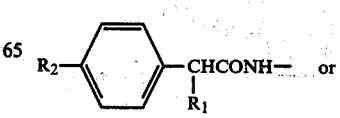

-continued (b)
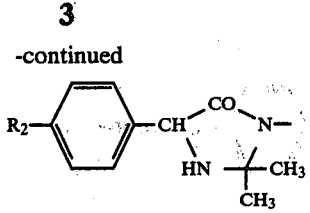

wherein R₁ is azido, amino, 1-methoxycarbonylpropen-2-ylamino or carbobenzyloxyamino and R₂ is hydrogen or hydroxy which comprises contacting one mole of a compound of the formula

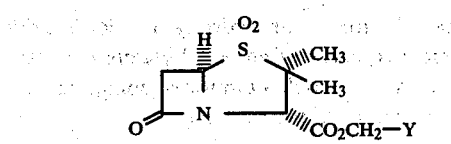

wherein Y is chloro, bromo or iodo with at least one mole of a compound of the formula

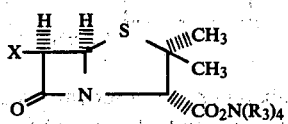

wherein R₃ is alkyl of one to four carbon atoms in a reaction-inert solvent at ambient temperatures.

A preferred feature of the process is the use of acetone or dimethylformamide as the reaction-inert solvent.

An especially preferred feature of this process is the preparation of those compounds wherein X is

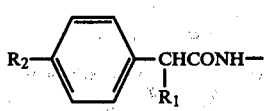

wherein R₂ is hydrogen, Y is iodo, R₃ is n-butyl and R₁ is azido, amino or 1-methoxycarbonylpropen-2-ylamino.

A third process of the present invention is for the preparation of compounds of the formula

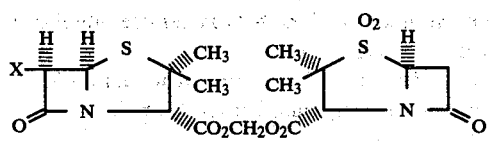

wherein X is

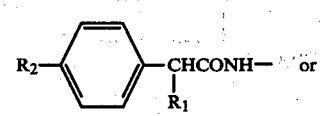  (a)

or

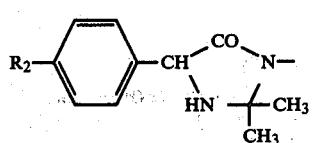  (b)

wherein R₁ is azido, amino, 1-methoxycarbonylpropen-2-ylamino or carbobenzyloxyamino and R₂ is hydrogen or hydroxy which comprises contacting one mole of a compound of the structure

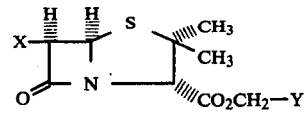

wherein Y is chloro, bromo or iodo with at least one mole of a compound of the formula

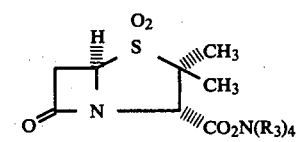

wherein R₃ is alkyl of one to four carbon atoms in a reaction-inert solvent at ambient temperatures.

A preferred feature of this process is the use of acetone or dimethylformamide as the reaction-inert solvent.

An especially preferred feature of this process is the preparation of those compounds wherein X is

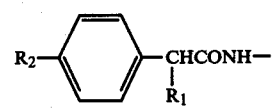

wherein R₂ is hydrogen, R₃ is n-butyl, Y is chloro and R₁ is azido, amino or 1-methoxycarbonylpropen-2-ylamino.

Those products of the second and third processes wherein R₂ is as defined and R₁ is azido, 1-methoxy-carbonylpropen-2-ylamino or carbobenzyloxyamino are useful intermediates to those compounds wherein R₁ is amino as taught by the herein described procedures. In addition, compounds of the structure wherein X is

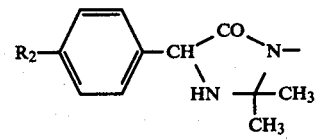

and R₂ is as defined contain a readily hydrolyzable ester moiety which in vivo gives a beta-lactam antibiotic and the beta-lactamase inhibitor penicillanic acid sulfone.

While U.K. application No. 2,044,255 teaches the coupling of chloroiodomethane with the potassium salt of penicillanic acid sulfone in the presence of a catalytic amount of tetrabutylammonium sulfate to give chloromethyl penicillanate sulfone, the processes of the present invention employ equimolar amounts of the tetraalkylammonium salts of the appropriate acid and requisite halide, and provide unexpectedly higher yields of the condensed products.

DETAILED DESCRIPTION OF THE INVENTION

The first process of the present invention is conveniently carried out by contacting one mole of a tetraalkylammonium salt of the formula

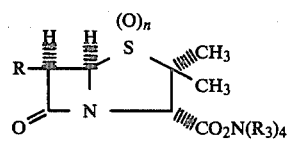

wherein R, n and $R_3$ are previously defined, with at least one mole of chloroiodomethane or bromochloromethane to provide the corresponding chloromethyl ester.

For each mole of tetraalkylammonium salt employed it is necessary for, optimum yields, to employ at least one equivalent of bromochloromethane or chloroiodomethane. In most instances it is preferred that a one to two fold excess of the theoretical amount of chloroiodomethane or bromochloromethane be employed. In practice, chloroiodomethane or bromochloromethane can be employed as the reactant as well as the solvent although other reaction-inert solvents can be employed in conjunction with the chloroiodomethane or bromochloromethane.

When the reaction is conducted in a reaction-inert solvent said solvent should be one which appreciably soulblizes the reactants without reacting to any greatextent with the reactants or products under the conditions of the reaction. It is preferred that said solvents have boiling and freezing point compatible with reaction temperature. Such solvents or mixtures thereof include halogenated hydrocarbons such as chloroform, carbontetrachloride and hexachloroethane and aromatic solvents such as toluene and xylene.

Reaction time is inherently dependent on concentration, reaction temperature and reactivity of the starting reagents. When the reaction is conducted at about $-20°$ C. to about 25° C. the reaction time for the formation of the product is about 18–0.5 hours.

On completion of the reaction the product can be isolated by chromatographing on a silica gel column.

As previously indicated, the products of this process are useful intermediates in preparing compounds with readily hydrolyzable esters which degrade in vivo into beta-lactam antibiotics and the beta-lactamase inhibitor penicillanic acid sulfone as taught in U.K. patent application No. 2,044,255 and U.S. Pat. No. 4,244,951.

The starting reagents for the aforedescribed process are either commercially available or are prepared by methods known from the literature or described herein.

The second process of the present invention is readily carried out by contacting one mole of a halomethyl ester of penicillanic acid sulfone of the formula

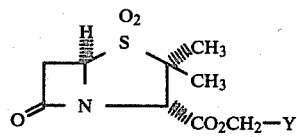

wherein Y is as previously defined, with at least one mole of a compound of the formula

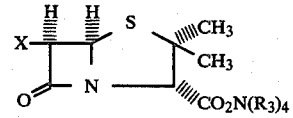

wherein X and $R_3$ are previously defined, in a reaction-inert solvent.

The criteria for a reaction-inert solvent for the second process of the present invention are similar to that for the first process. Said solvents or mixtures thereof should solubilize the reactants without reacting to any appreciable extent with either the reactants or the product under the conditions of the reaction. The preferred solvent for said reaction is acetone, although a wide variety of other aprotic, water-miscible solvents including ethyl acetate, acetonitrile, dimethylformamide and hexamethylphosphoramide are also operable.

Reaction time is dependent on concentration, reaction temperature and reactivity of the starting reagents. When the reaction is conducted at the preferred temperature of about 25° C. the reaction is usually complete in 30–60 minutes.

For optimum yield of product at least one mole of the tetraalkylammonium salt is employed per mole of halomethyl ester. In addition, as much as a 10–20% excess of the salt can be employed without markedly affecting the quality of the product produced.

On completion of the reaction the solvent is removed, usually in vacuo, and the residual product is purified by chromatographing on silica gel.

The tetraalkylammonium penicillanate salts and the halomethyl penicillanate sulfones are prepared by the herein described procedures.

The third process of the present invention is carried out by contacting one mole of a halomethyl penicillanate of the formula

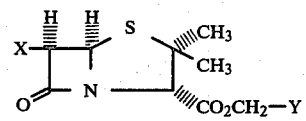

wherein X and Y are as previously defined, with at least one mole of a compound of the formula

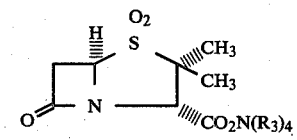

wherein $R_3$ is as previously defined.

The reaction is carried out in a reaction-inert solvent, which should solubilize the reactants without reacting to any appreciable extent with either the reactants or the product under the conditions of said reaction. The preferred solvent for this reaction is acetone, although other highly polar water miscible, aprotic solvents, such as dimethylformamide and hexamethyl phosphoramide, can also be employed.

Reaction time is a function of concentration, temperature and reactivity of the starting reagents. Reaction is conducted at 0° C. to 60° C. with a preferred temperature of about 25° C. to about 60° C. The reaction time for the preferred temperature is about 0.5–4 hours. For convenience, the reaction is frequently allowed to proceed overnight without a detrimental affect on the product.

On completion of the reaction it is diluted with water and a water-immiscible solvent. The organic phase is concentrated and the product purified by column chromatography.

As previously indicated, the compounds of the second and third processes of the present invention of the formula

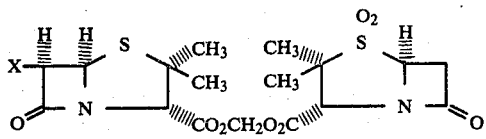

wherein X is

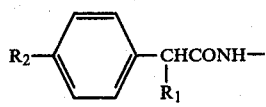

where $R_2$ is as defined and $R_1$ is amino, when administered to a host suffering from a bacterial infection are readily hydrolyzed into a beta-lactam antibiotic and the beta-lactamase inhibitor penicillanic acid sulfone. Those compounds of these processes, of the above formula, wherein $R_2$ is as defined and $R_1$ is azido, 1-methoxycarbonylpropen-2-ylamino or carbobenzyloxyamino are useful intermediates which can be converted to those compounds wherein $R_1$ is amino.

Reduction of those compounds of the above formula wherein $R_1$ is azido can be carried out by shaking the intermediate dissolved in an appropriate solvent or solvents, such as a lower alkanol and methylene chloride in the presence of a catalytic amount of a noble metal, such as palladium-on-charcoal, in a hydrogen atmosphere at an initial pressure of about 10–50 psi. On completion of the reduction the spent catalyst is filtered and filtrate concentrated to give the desired product.

Similarly, those compounds of this process wherein $R_1$ is carbobenzyloxyamino can be reduced to provide those products wherein $R_1$ is amino. The hydrogenolysis reaction is readily carried out by shaking a mixture of the intermediate, dissolved in a lower alkanol and methylene chloride, and a catalytic amount of a noble metal in a hydrogen atmosphere at an initial pressure of 5–50 psi. On completion of the reaction the catalyst is filtered and the product isolated from the filtrate by evaporation.

Compounds of the above structure wherein $R_1$ is amino can be obtained from those wherein $R_1$ is 1-methoxycarbonylpropen-2-ylamino by treatment of a solution of the latter with at least an equivalent amount of an acid. If a non-aqueous reaction inert solvent, such as ethyl acetate, is employed it is preferred that at least 1–5% (v:v) of water be present in said solvent in order to facilitate the hydrolysis of the enimine. Acids suitable for the hydrolysis include inorganic mineral acids as well as organic sulfonic acids. The hydrolysis product is isolated as the corresponding acid addition salt by filtration from the reaction solvent.

As previously mentioned, U.K. patent application No. 2,044,255 teaches that the halomethyl penicillanate sulfones, products of the presently claimed process, can be coupled with a variety of beta-lactam antibiotics to provide in vivo antibacterial agents which result from the absorption and subsequent hydrolysis of the coupled product to give high blood and tissue levels of penicillanic acid sulfone and the beta-lactam antibiotic resulting from said hydrolysis. In addition, the aforementioned U.K. application teaches how to use the products resulting from a coupling of penicillanic acid sulfone and a beta-lactam antibiotic.

The following examples are provided solely for the purpose of further illustration. Nuclear magnetic resonance spectra (NMR) were measured at 60 MHz for solutions in deuterochloroform ($CDCl_3$), perdeutero dimethyl sulfoxide (DMSO-$d_6$) or deuterium oxide ($D_2O$) or are noted otherwise, and peak positions are expressed in parts per million (ppm) downfield from tetramethylsilane or sodium 2,2-dimethyl-2-silapentane-5-sulfonate. The following abbreviations for peak shapes are used: b, broad; s, singlet; d, doublet; t, triplet; q, quartet; m, multiplet.

EXAMPLE 1

Chloromethyl 6-(2,2-dimethyl-5-oxo-4-phenyl-1-imidazolidinyl)-penicillanate

To a suspension of 1.56 g. of 6-(2,2-dimethyl-5-oxo-4-phenyl-1-imidazolidinyl) penicillanic acid [J. Org. Chem., 31, 897 (1966)] in 20 ml. of methylene chloride and 20 ml. of water was added sufficient tetrabutylammonium hydroxide to give a pH of 8.5. The organic layer was separated and the aqueous washed (2×20 ml.) with methylene chloride. The organic layers were combined, dried over sodium sulfate and concentrated to give 2.3 g. of a foam.

The residual tetrabutylammonium salt was added to 15 ml. of chloroiodomethane and the reaction mixture allowed to stir at room temperature overnight. The reaction mixture was chromatographed on 100 g. of silica gel using ethyl acetate/hexane (1:1 v:v) as the eluent, taking 14 ml. cuts every 30 sec. Cuts 195–230 were combined and concentrated to dryness to give 440 mg. of the desired product.

The NMR spectrum ($CDCl_3$) showed absorption at 1.5 (s, 3H), 1.58 (s, 6H), 1.72 (s, 3H), 4.58 (s, 1H), 4.67 (s, 1H), 4.73 (d, 1H), 5.54 (d, 1H) and 7.2–7.6 (m, 5H) ppm.

Using the same procedure, and starting with 6-(2,2-dimethyl-5-oxo-4-[p-hydroxyphenyl]-1-imidazolidinyl)-penicillanic acid [J. Chem. Soc., 1920 (1971)], chloromethyl 6-(2,2-dimethyl-5-oxo-4-[p-hydroxyphenyl]-1-imidazolidinyl)penicillanate is prepared.

EXAMPLE 2

Chloromethyl 6-(alpha-aminophenylacetamido)penicillanate

A suspension of 4.03 g. of 6-(alpha-aminophenylacetamido)penicillanic acid trihydrate in 30 ml. of methylene chloride and 30 ml. of water was treated with sufficient tetrabutylammonium hydroxide to give a pH of 8.5. The methylene chloride layer was separated and the aqueous further extracted (2×30 ml.) with fresh methylene chloride. The organic extracts were combined, dried over sodium sulfate and concentrated in vacuo to give 6.0 g. the desired tetrabutylammonium salt.

Five and three-tenths grams of the above salt was added to 35 ml. of chloroiodomethane and the resulting reaction mixture allowed to stir at room temperature for 3 hours. The reaction was chromatographed on 200 g. of silica gel using ethyl acetate as the eluent, and taking 10 ml. cuts every 0.8 min. Cuts 115–139 were combined and concentrated in vacuo to a white foam.

The NMR spectrum (CDCl$_3$) showed absorption at 1.55 (s, 3H), 1.65 (s, 3H), 2.6–3.2 (s, 2H), 4.42 (s, 1H), 5.3–5.8 (m, 3H), 5.7 (dd, 2H), 7.3 (s, 5H) and 7.9 (d, 1H) ppm.

Starting with the tetramethylammonium salt of 6-(alpha-amino-p-hydroxyphenylacetamido)penicillanic acid, and employing the above procedure, chloromethyl 6-(alpha-amino-p-hydroxyphenylacetamido)penicillanate is prepared.

EXAMPLE 3

Chloromethyl 6-(alpha-azidophenylacetamido)penicillanate

A mixture of 3.97 g. of 6-(alpha-azidophenylacetamido)penicillanic acid sodium salt in 75 ml. of ethyl acetate and 35 ml. of water was treated with sufficient 6 N hydrochloric acid to give a pH of 1.7. The organic phase was separated and the aqueous layer further extracted (2×50 ml.) with fresh ethyl acetate. The ethyl acetate layers were combined, dried over sodium sulfate and concentrated under vacuum to give 3.8 g. of a foam. The residue was taken up in 50 ml. of methylene chloride to which was added 35 ml. of water. The pH was adjusted to 8.5 with 40% aqueous tetrabutylammonium hydroxide, and organic phase separated. The aqueous was further extracted with fresh methylene chloride (2×50 ml.) and the combined organic layers dried over sodium sulfate and concentrated to give 6.2 g. of the desired tetrabutylammonium salt.

In a flask fitted with a magnetic stirrer and stopper were combined 6.2 g. of tetrabutylammonium 6-(alpha-azidophenylacetamido)penicillanate and 35 ml. of chloroiodomethane, and the reaction mixture allowed to stir at room temperature overnight. The reaction mixture was chromatographed on 40 g. of silica gel using ethyl acetate/hexane (1:1 v:v) as the eluent, 12 ml. cuts being taken every 36 sec. Cuts 34–68 were combined and concentrated in vacuo to give 4.05 g. of the desired product as a light yellow oil.

The NMR spectrum (CDCl$_3$) showed absorption at 1.58 (s, 3H), 1.68 (s, 3H), 4.45 (s, 1H), 5.1 (s, 1H), 5.5–5.9 (dd m, 4H), 7.2 (d, 1H) and 7.4 (s, 5H) ppm.

The above procedure is repeated, starting with sodium 6-(alpha-azido-p-hydroxyphenylacetamido)penicillanate and tetrapropylammonium hydroxide to give chloromethyl 6-(alpha-azido-p-hydroxyphenylacetamido)penicillanate.

EXAMPLE 4

Chloromethyl penicillanic acid 1,1-dioxide

A mixture of 4.66 g. of penicillanic acid 1,1-dioxide in 50 ml. of methylene chloride and 35 ml. of water was treated with sufficient tetrabutylammonium hydroxide (40% in water) to give a pH of 6.0. The methylene chloride layer was separated and the aqueous phase extracted with fresh methylene chloride (2×50 ml.). The organic layers were combined, dried over sodium sulfate and concentrated to give 10.1 g. of the desired intermediate.

The above tetrabutylammonium penicillanate sulfone was added to 50 ml. of chloroiodomethane and the reaction mixture allowed to stir at ambient temperatures overnight. The reaction mixture was concentrated to half volume in vacuo, and chromatographed on 200 g. of silica gel using ethyl acetate/hexane as the eluent, 12 ml. cuts being taken every 30 sec. Fractions 41–73 were combined and concentrated to dryness to give 3.2 g. of the desired product.

The NMR spectrum (CDCl$_3$) showed absorption at 1.5 (s, 3H), 1.66 (s, 3H), 3.42 (d, 2H), 4.38 (s, 1H), 4.6 (t, 1H) and 5.7 (dd, 2H) ppm.

EXAMPLE 5

Chloromethyl 6-alpha-carbobenzyloxyamino-p-hydroxyphenylacetamido)penicillanate

To 12.57 g. of 6-(alpha-amino-p-hydroxyphenylacetamido)penicillanic acid trihydrate in 75 ml. of water and 75 ml. of acetone cooled to 0° C. was added sufficient 2 N sodium hydroxide solution to give a pH of 8.5. To the resulting hazy solution was added dropwise 4.28 ml. of carbobenzyloxy chloride over a 5 min. period. The pH of 8.0 was maintained by the periodic addition of 2 N sodium hydroxide. After 20 min. the reaction mixture was extracted with diethyl ether (2×150 ml.), the aqueous layer over-layed with ethyl acetate and the pH adjusted to 1.5 with 6 N hydrochloric acid. The ethyl acetate layer is separated, washed successively with water (2×50 ml.) and dried over sodium sulfate. The solvent is removed in vacuo to give the desired 6-(alpha-carbobenzyloxyaminophenylacetamido)penicillanic acid intermediate.

One gram of the above intermediate in 30 ml. of methylene chloride and 20 ml. of water was treated with sufficient tetrabutylammonium hydroxide (40% in water) until the pH was 8.0. The organic phase was separated and the aqueous layer extracted with fresh methylene chloride (2×30 ml.). The methylene chloride extracts were combined, dried over sodium sulfate and concentrated in vacuo to give 1.4 g. of the corresponding tetrabutylammonium salt.

One gram of the above salt is added to 7.5 ml. of chloroiodomethane and the resulting reaction mixture allowed to stir at room temperature overnight. The reaction mixture is chromatographed on 25 g. of silica gel using ethyl acetate/hexane (1:0.5 v:v), cuts of 10 ml. being taken every 30 sec. The cuts containing the product are combined and concentrated under vacuum to give the requisite chloromethyl 6-[alpha-carbobenzyloxyamino-p-hydroxyphenylacetamido]penicillanate.

In a similar manner, starting with 6-(alpha-aminophenylacetamido)penicillanic acid and tetramethylammonium hydroxide, chloromethyl 6-(alpha-carbobenzyloxyaminophenylacetamido)penicillanate is prepared.

EXAMPLE 6

Iodomethyl penicillanate 1,1-dioxide

To a solution of 7.9 g. of chloromethyl penicillanate 1,1-dioxide in 100 ml. of dry acetone maintained under a nitrogen atmosphere was added 21.0 g. of sodium iodide, and the reaction mixture allowed to stir overnight at room temperature. The reaction was concentrated in vacuo, and the residue was dissolved in 150 ml. ethyl acetate and 150 ml. water. The organic layer was separated and the aqueous extracted with fresh ethyl acetate. The organic extracts were combined, washed with water (1×50 ml.) and brine (1×50 ml.) and dried over sodium sulfate. Removal of the solvent gave 10.5 g. of product, m.p. 100°–102° C.

The NMR spectrum (CDCl$_3$) showed absorption at 1.55 (s, 3H), 1.68 (s, 3H), 3.5 (d, 2H), 4.4 (s, 1H), 4.65 (t, 1H) and 6.0 (dd, 2H) ppm.

EXAMPLE 7

6'-(alpha-Amino-p-hydroxyphenylacetamide)penicillanoyloxymethyl penicillanate 1,1-dioxide

A.

6'-(alpha-carbobenzyloxyamino-p-hydroxyphenylphenylacetamido)penicillanoyloxymethyl penicillanate 1,1-dioxide To 9.5 g. of tetrabutylammonium 6-(alpha-carbobenzyloxyamino-p-hydroxyphenylacetamido)penicillanate in 50 ml. of dry acetone was added 4.78 g. of iodomethyl penicillanate 1,1-dioxide, and the reaction mixture allowed to stir at room temperature for 30 min. The reaction mixture was concentrated in vacuo and chromatographed on 200 g. of silica gel using ethyl acetate/methylene chloride (1:1 v:v), 25 ml. cuts being made. Fractions 29–49 were combined and concentrated to give 6.5 g. of the desired product as a yellow foam.

The NMR spectrum (DMSO-D$_6$) showed absorption at 1.42 (s, 3H), 1.52 (s, 3H), 1.6 (s, 3H), 3.1–3.9 (m, 2H), 4.45 (s, 1H), 4.58 (s, 1H), 5.08 (s, 2H), 4.98–5.7 (m, 4H), 5.95 (s, 2H), 6.68 (d, 2H), 7.2 (d, 2H) and 7.35 (s, 5H) ppm.

B.

6'-(alpha-amino-p-hydroxyphenylacetamido)penicillanoyloxymethyl penicillanate 1,1-dioxide To 6.4 g. of 6'-(alpha-carbobenzyloxyamino-p-hydroxyphenylacetamido)penicillanoyloxymethyl penicillanate 1,1-dioxide in 70 ml. of methylene chloride and 70 ml. of isopropanol was added 6.5 g. of 10% palladium-on-charcoal and the resulting mixture shaken in a hydrogen atmosphere at an initial pressure of 50 psi for 45 min. An additional 3.0 g. of catalyst was added and the hydrogenation continued for 30 min. This procedure of adding 3.0 of catalyst was repeated three times. The reaction was filtered and spent catalyst was washed with methylene chloride/isopropanol (1:1 v:v). The filtrate and washings were combined and concentrated to near dryness. Diethyl ether (200 ml.) was added to the white suspension and the mixture allowed to stir for 15 min. The solids were filtered and dried to give 4.9 g. of product. The solids were dissolved in 35 ml. of dimethylformamide and added dropwise to 1500 ml. of chloroform. The precipitated solids were filtered and dried, 2.35 g. Additional second crop product was isolated by diluting the filtrate with 2 l. of hexane, 1.75 g.

The NMR spectrum (DMSO-D$_6$) showed absorption at 1.42 (s, 6H), 1.55 (s, 6H), 3.1–3.95 (m, 2H), 4.42 (s, 1H), 4.57 (s, 1H), 4.9–5.3 (m, 2H), 5.4–5.75 (m, 2H), 5.95 (s, 2H), 6.82 (d, 2H), 7.35 (d, 2H) and 8.7–9.7 (m, 3H) ppm.

C.

6'-(alpha-amino-p-hydroxyphenylacetamido)penicillanoyloxymethyl penicillanate 1,1-dioxide hydrochloride To 35 ml. of 0.1 N hydrochloric acid cooled to 0° C. was added 2.15 g. of 6'-(alpha-amino-p-hydroxyphenylacetamido)penicillanoyloxymethyl penicillanate 1,1-dioxide. The solution was filtered and freeze dried to give 2.1 g. of the desired product.

The NMR spectrum (DMSO-D$_6$) showed absorption at 1.38 (s, 6H), 1.48 (s, 6H), 3.0–3.9 (m, 2H), 4.38 (s, 1H), 4.48 (s, 1H), 4.9–5.2 (m, 2H), 5.38–5.64 (m, 2H), 5.84 (s, 2H), 6.7 (d, 2H), 7.24 (d, 2H), 8.3–9.2 (bs, 4H) and 9.4 (d, 1H) ppm.

In a similar manner, following the procedures of Example 7A-C and starting with tetramethylammonium 6-(alpha-carbobenzyloxyaminophenylacetamido)penicillanate and iodomethyl penicillanate 1,1-dioxide, 6'-(alpha-aminophenylacetamido)penicillanoyloxymethyl penicillanate 1,1-dioxide hydrochloride is produced.

EXAMPLE 8

6'-(alpha-Aminophenylacetamido)penicillanoyloxymethyl penicillanate 1,1-dioxide

A.

6'-(alpha-azidophenylacetamido)penicillanoyloxymethyl penicillanate 1,1-dioxide

To a slurry of 5.0 g. of tetrabutylammonium 6-(alpha-azidophenylacetamido)penicillanate in 75 ml. of acetone under a nitrogen atmosphere was added 3.0 g. of iodomethyl penicillanate 1,1-dioxide in 20 ml. of acetone, and the resulting reaction mixture allowed to stir at room temperature for 30 minutes. The reaction mixture was concentrated to a yellow oil, which was chromatographed on 80 g. of silica gel using ethyl acetate/methylene chloride (1:4 v:v) as the eluent. Fractions comprised of 75 ml. were collected. Fractions 2–6 were combined and concentrated in vacuo to give the desired compound, 4.53 g.

The NMR spectrum (CDCl$_3$) showed absorption at 1.44 (s, 3H), 1.52 (s, 3H), 1.6 (s, 3H), 1.66 (s, 3H), 3.4 (d, 2H), 4.4 (s, 1H), 4.46 (s, 1H), 4.6 (t, 1H), 5.1 (s, 1H), 5.4–5.7 (m, 2H), 5.88 (s, 2H), 7.18 (d, 1H) and 7.37 (s, 5H) ppm.

B.

6'-(alpha-aminophenylacetamido)penicillanoyloxymethyl penicillanate 1,1-dioxide

A mixture of 500 mg. of 6'-(alpha-azidophenylacetamido)penicillanoyloxymethyl penicillanate 1,1-dioxide and 500 mg. of 10% palladium-on-charcoal in 25 ml. of isopropanol and 12 ml. of methylene chloride was shaken in a hydrogen atmosphere at an initial pressure of 50 psi at room temperature. After 30 min. the reaction mixture was filtered and the filtrate concentrated to give 362 mg. of desired product as an amorphous solid.

The NMR spectrum (CDCl$_3$) showed absorption at 1.5 (d, 6H), 1.6 (d, 6H), 3.55 (d, 2H), 4.45 (s, 1H), 4.55 (s, 1H), 4.6–4.75 (m, 2H), 5.5–5.7 (m, 2H), 5.9 (q, 2H), 7.4 (s, 4H) and 8.1 (d, 1H, J=6 Hz) ppm.

In a similar manner, starting with tetrapropylammonium 6-(alpha-azido-p-hydroxyphenylacetamido)penicillanate and chloromethyl penicillanate 1,1-dioxide and following the procedures of Example 8A-B, 6'-(alpha-aminophenylacetamido)penicillanoyloxymethyl penicillanate 1,1-dioxide is prepared.

EXAMPLE 9

6'-(alpha-Aminophenylacetamido)penicillanoyloxymethyl penicillanate 1,1-dioxide

To 3.1 g. of tetrabutylammonium 6-(alpha-aminophenylacetamido)penicillanate in 20 ml. of ethyl acetate and 5 ml. of methylene chloride was added 2.0 g. of iodomethyl penicillanate 1,1-dioxide in 10 ml. of ethyl acetate, and the reaction mixture allowed to stir at room temperature for 30 min. The methylene chloride was removed in vacuo and the resulting suspension filtered. The filtrate was treated with 25 ml. of water and the pH adjusted to 2.5 with 1 N hydrochloric acid. The aqueous layer was retained and organic phase again extracted with fresh water at pH 2.5. The aqueous layers were combined, saturated with salt and extracted with methylene chloride. The organic phase was separated, dried over sodium sulfate and concentrated under vacuum to about 10 ml. The residual solution was then added to diethyl ether with stirring, and the resulting precipitate filtered and dried, 370 mg. The product was indistinguishable from that isolated in Example 8B.

Starting with tetramethylammonium 6-(alpha-amino-p-hydroxyphenylacetamido)penicillanate and chloromethyl penicillanate 1,1-dioxide, and employing the above procedure of Example 9, 6'-(alpha-amino-p-hydroxyphenylacetamido)penicillanoyloxymethyl penicillanate 1,1-dioxide is prepared.

EXAMPLE 10

6'-(2,2-Dimethyl-5-oxo-4-phenyl-1-imidazolidinyl)-penicillanoyloxymethyl penicillanate 1,1-dioxide A solution of 470 mg. of chloromethyl penicillanate 1,1-dioxide in 7 ml. of ethyl acetate is added all at once to a solution of 1.0 g. of tetrabutylammonium 6-(2,2-dimethyl-5-oxo-4-phenyl-1-imidazolidinyl)penicillanate in 10 ml. of ethyl acetate and 3 ml. of methylene chloride, and the resulting reaction mixture allowed to stir at ambient temperatures for 45 min. The reaction mixture is washed successively with water and a saturated brine solution and dried over sodium sulfate. The organic phase is then chromatographed on 75 g. of silica gel using ethyl acetate/hexane (1:1 v:v) as the eluent, 14 ml. cuts being taken every 30 sec. Fractions 195–230 are combined and concentrated to give the desired product.

By a similar procedure, starting with 646 mg. of tetrabutylammonium 6-(2,2-dimethyl-5-oxo-4-[p-hydroxyphenyl]-1-imidazolidinyl)penicillanate and 281 mg. of iodomethyl penicillanate 1,1-dioxide, 210 mg. of 6'-(2,2-dimethyl-5-oxo-4-[p-hydroxyphenyl]-1-imidazolidinyl)-penicillanoyloxymethyl penicillanate 1,1-dioxide was prepared.

The NMR spectrum (CDCl$_3$) showed absorption at 1.4–1.8 (m, 18H), 3.48 (d, 2H), 4.4–4.9 (m, 5H), 5.56 (d, 1H), 5.9 (s, 2H), 6.64 (d, 2H) and 7.18 (d, 2H) ppm.

EXAMPLE 11

6'-(alpha-Azidophenylacetamido)penicillanoyloxymethyl penicillanate 1,1-dioxide

To 5 ml. of dry dimethylformamide was added 424 mg. of chloromethyl 6-(alpha-azidophenylacetamido)-penicillanate followed by 474 mg. of tetrabutylammonium penicillanate 1,1-dioxide, and the resulting reaction mixture allowed to stir at room temperature overnight. The reaction mixture was diluted with 50 ml. of ethyl acetate and subsequently washed with water (3×15 ml.) and a saturated salt solution (1×15 ml.). The organic phase was dried over sodium sulfate and concentrated to a foam, which was subsequently chromatographed on 40 g. of silica gel using methylene chloride/ethyl acetate (4:1 v:v) as the eluent, 8 ml. fractions being collected every 30 sec. Fractions 13–29 were combined and concentrated in vacuo to give 320 mg. of the desired product which was indistinguishable from the product prepared in Example 8A.

EXAMPLE 12

Starting with the appropriate chloromethyl 6-substituted penicillanate from Examples 1–5 and a tetraalkylammonium penicillanate 1,1-dioxide and employing the procedure of Example 11, the following compounds are prepared:

6'-(alpha-azido-p-hydroxyphenylacetamido)penicillanoyloxymethyl penicillanate 1,1-dioxide;
6'-(alpha-carbobenzyloxyaminophenylacetamido)-penicillanoyloxymethyl pencillanate 1,1-dioxide;
6'-(alpha-carbobenzyloxyamino-p-hydroxy-phenylacetamido)penicillanoyloxymethyl penicillanate 1,1-dioxide;
6'-(alpha-aminophenylacetamido)penicillanoyloxymethyl penicillanate 1,1-dioxide;
6'-(alpha-amino-p-hydroxyphenylacetamido)penicillanoyloxymethyl penicillanate 1,1-dioxide;
6'-(2,2-dimethyl-5-oxo-4-phenyl-1-imidazolidinyl)-penicillanoyloxymethyl penicillanate 1,1-dioxide; and
6'-(2,2-dimethyl-5-oxo-4-[p-hydroxyphenyl]-1-imidazolidinyl)penicillanoyloxymethyl penicillanate 1,1-dioxide.

EXAMPLE 13

6'-(alpha-Aminophenylacetamido)penicillanoyloxymethyl penicillanate 1,1-dioxide p-toluene sulfonate

A.

6'-(alpha-N-[1-methoxycarbonylpropen-2-yl]aminophenylacetamido)penicillanoyloxymethyl penicillanate 1,1-dioxide To 125 ml. of methylene chloride and 50 ml. of water was added 8.06 g. of 6-(alpha-aminophenylacetamido)-penicillanic acid trihydrate and the pH adjusted to 8.5 by the addition of a 40% tetrabutylammonium hydroxide solution in water. The methylene chloride layer was separated and the aqueous layer was extracted with fresh methylene chloride (2×30 ml.). The methylene chloride layers were combined and dried over magnesium sulfate.

The mixture was filtered and the filtrate concentrated in vacuo. Chloroform (300 ml.), methyl acetoacetate (2.16 ml.) and magnesium sulfate (20 g.) was added to the residue and the mixture heated to reflux for 30 minutes. The magnesium sulfate was filtered and the filtrate concentrated under reduced pressure to give a yellow foam. Treatment of the residue with 150 ml. of ethyl acetate gave a white solid which was filtered, washed with ethyl acetate (3×25 ml.) and diethyl ether (2×50 ml.) and dried under nitrogen to give 6.5 g. of the tetrabutylammonium 6-(alpha-1-methoxycarbonylpropen-2-ylaminophenylacetamido)penicillanate.

To 1.38 g. of the above tetrabutylammonium salt in 10 ml. of dry acetone was added 1.04 g. of iodomethyl penicillanate 1,1-dioxide, and the mixture allowed to stir for 10 minutes at room temperature. The mixture was concentrated in vacuo and the residue chromatographed on 75 g. of silica gel using ethyl acetate/hexane (1:1, v:v) as the eluent, 10 ml. fractions being taken every 9 minutes. Fractions 11–19 were combined and concentrated under vacuum to give 970 mg. of the desired product.

The NMR spectrum (CDCl$_3$) showed absorption at 1.42 (s, 3H), 1.48 (s, 3H), 1.55 (s, 3H), 1.6 (s, 3H), 1.9 (s, 3H), 3.48 (d, 2H), 3.66 (s, 3H), 4.43 (s, 1H), 4.46 (s, 1H), 4.56–4.7 (m, 2H), 5.13 (d, 1H), 5.4–5.75 (m, 2H), 5.9 (s, 2H), 6.78 (d, 1H), 7.42 (s, 5H) and 9.38 (d, 1H) ppm.

B.

6'-(alpha-aminophenylacetamido)penicillanoyloxymethyl penicillanate 1,1-dioxide p-toluenesulfonate To 346 mg. of 6'-(alpha-N-[1-methoxycarbonylpropen-2-yl]aminophenylacetamido)penicillanoyloxymethyl penicillanate 1,1-dioxide in 20 ml. of ethyl acetate was added 95 mg. of p-toluenesulfonic acid hydrate in 5 ml. of ethyl acetate and 0.5 ml. of water. After several minutes the precipitate which formed was filtered, washed with ethyl acetate and dried, 290 mg.

The NMR spectrum (DMSO-$D_6$) showed absorption at 1.38 (s, 6H), 1.5 (s, 6H), 2.3 (s, 3H), 3.05–3.9 (m, 2H), 4.4 (s, 1H), 4.5 (s, 1H), 4.95–5.3 (m, 2H), 5.35–5.7 (m, 2H), 5.9 (s, 2H), 7.08 (d, 2H), 7.55 (d, 2H), 7.44 (d, 2H), 8.6–9.0 (ds, 3H) and 9.4 (d, 1H) ppm.

EXAMPLE 14

6'-(alpha-Amino-p-hydroxyphenylacetamido)-penicillanoyloxymethyl penicillanate 1,1-dioxide hydrochloride

A.

6'-(alpha-N-[1-methoxycarbonylpropen-2-yl]amino-p-hydroxyphenylacetamido)penicillanoyloxymethyl penicillanate 1,1-dioxide To 300 ml. of methylene chloride was added 41.9 g. of 6-(alpha-amino-p-hydroxyphenylacetamido)penicillanic acid and 50 ml. of water, and the pH adjusted to 8.5 with 40% aqueous tetrabutylammonium hydroxide. The mixture was placed in a separatory funnel and the aqueous layer removed, saturated with sodium sulfate and extracted with methylene chloride from the separatory funnel and the methylene chloride extracts were combined, dried over sodium sulfate and concentrated to an oil which crystallized on trituration with acetone to give 44.6 g. of tetrabutylammonium 6-(alpha-amino-p-hydroxyphenylacetamido)penicillanate.

The above salt was added to 150 ml. of methyl acetoacetate, and the suspension heated at steam bath temperature for 8 minutes. The mixture was allowed to cool, and the resulting precipitate was filtered and washed with methyl acetoacetate (3×25 ml.) and diethyl ether, 49.25 g.

To 47.5 g. of the above salt in 250 ml. of dimethylformamide at 0° C. was added with stirring 18.26 g. of iodomethyl penicillanate 1,1-dioxide in 50 ml. of the same solvent was added over a 20 minute period. Ten minutes after completion of the addition the reaction mixture was poured into 3 l. of ethyl acetate and the resulting precipitate was filtered. The precipitate was washed with ethyl acetate (100 ml.) of the washings combined ethyl acetate was washed successively with a brine solution (4×500 ml.), water (4×500 ml.) and a brine solution (2×500 ml.) and dried over sodium sulfate. The residue remaining after the solvent was removed was chromatographed over 750 g. of silica gel using ethyl acetate as the eluent. The fractions (250 ml. each) 2–5 were combined and concentrated to give the product, 31.2 g.

The NMR spectrum (DMSO-$D_6$, $^1$H 100.1 M Hz) showed absorption at 1.37 (s, 3H), 1.38 (s, 3H), 1.48 (s, 3H), 1.57 (s, 3H), 1.76 (s, 3H), 3.14–3.82 (m, 2H), 3.51 (s, 3H), 4.42 (s, 1H), 4.44 (s, 1H), 4.54 (s, 1H), 5.1–5.22 (m, 1H), 5.3–5.64 (m, 3H), 5.9 (s, 2H), 6.7 (d, 2H), 7.14 (d, 2H), 9.02 (d, 1H), 9.24 (d, 1H) and 9.34–9.54 (bs, 1H) ppm.

B.

6'-(alpha-amino-p-hydroxyphenylacetamido)penicillanoyloxymethyl penicillanate 1,1-dioxide hydrochloride To 31.1 g. of 6'-(alpha-N-[1-methoxycarbonylpropen-2-yl]amino-p-hydroxyphenylacetamido)penicillanate 1,1-dioxide in 250 ml. of acetone cooled to 0° C. was added 439 ml. of 0.1 N hydrochloric acid. After 5 minutes of stirring the acetone was removed in vacuo and the aqueous was extracted with diethyl ether (3×700 ml.). The aqueous layer was separated, filtered through super cel and freeze dried to give 23.1 g. of the desired product.

The NMR spectrum (DMSO-$D_6$) showed absorption at 1.38 (s, 6H), 1.48 (s, 6H), 3.0–3.9 (m, 2H), 4.38 (s, 1H), 4.48 (s, 1H) 4.9–5.2 (m, 2H), 5.35–5.64 (m, 2H), 5.87 (s, 2H), 6.7 (d, 2H), 7.24 (d, 2H), 8.3–9.2 (bs, 4H) and 9.4 (d, 1H) ppm.

EXAMPLE 15

6'-(alpha-Aminophenylacetamido)penicillanoyloxymethyl penicillanate 1,1-dioxide p-toluenesulfonate

A.

chloromethyl 6-(alpha-1-methoxycarbonylpropen-2-ylaminophenylacetamido)penicillanate To 125 ml. of methylene chloride and 50 ml. of water was added 8.06 g. of 6-(alpha-aminophenylacetamido)-penicillanic acid trihydrate and the pH adjusted to 8.5 by the addition of a 40% tetrabutylammonium hydroxide solution in water. The methylene chloride layer was separated and the aqueous layer was extracted with fresh methylene chloride (2×30 ml.). The methylene chloride layers were combined and dried over magnesium sulfate.

The mixture was filtered and the filtrate concentrated in vacuo. Chloroform (300 ml.), ethyl acetoacetate (2.16 ml.) and magnesium sulfate (20 g.) was added to the residue and the mixture heated to reflux for 30 minutes. The magnesium sulfate was filtered and the filtrate concentrated under reduced pressure to give a yellow foam. Treatment of the residue with 150 ml. of ethyl acetate gave a white solid which was filtered, washed with ethyl acetate (3×25 ml.) and diethyl ether (2×50 ml.) and dried under nitrogen to give 6.5 g. of the tetrabutylammonium 6-(alpha-1-methoxycarbonylpropen-2-ylaminophenylacetamido)penicillanate.

To 15 ml. of chloroiodomethane was added 1.38 g. of the tetrabutylammonium salt, and the resulting mixture allowed to stir for one hour at room temperature. The reaction solution was subsequently chromatographed on 75 g. silica gel using ethyl acetate/hexane (1:1, v:v) as the eluent, 50 ml. cuts being made. Fractions 4–6 were combined and concentrated to give 800 mg. of the desired product.

The NMR spectrum (CDCl$_3$) showed absorption at 1.5 (s, 3H), 1.57 (s, 3H), 1.9 (s, 3H), 3.65 (s, 3H), 4.4 (s, 1H), 4.65 (s, 1H), 5.12 (d, 1H), 5.42–5.7 (m, 2H), 5.75 (dd, 2H), 6.8 (d, 1H), 7.4 (s, 5H) and 9.35 (d, 1H) ppm.

B.

6'-(alpha-Aminophenylacetamido)penicillanoyloxymethyl penicillanate 1,1-dioxide p-toluenesulfonate A mixture of 496 mg. of chloromethyl 6-(alpha-1-methoxycarbonylpropen-2-ylaminophenylacetamido)-penicillanate and 750 mg. of sodium iodide in 10 ml. of acetone was allowed to stir at room temperature overnight. The solvent was removed in vacuo and the residue extracted with 40 ml. of ethyl acetate. The extract was washed successively with water (3×10 ml.) and an aqueous saturated sodium chloride solution (2×5 ml.), and then dried over sodium sulfate. The oil remaining (700 mg.) after the solvent was removed was triturated with petroleum ether to give iodomethyl 6-(alpha-1-methoxycarbonylpropen-2-ylaminophenylacetamido)-penicillanate as a solid.

A mixture of 590 mg. of iodomethyl 6-(alpha-1-methoxycarbonylpropen-2-ylaminoacetamido)penicillanate and 474 mg. of tetrabutylammonium penicillanate sulfone was allowed to stir in 10 ml. of acetone for 20 minutes. The reaction mixture was concentrated to dryness and the residue treated with 40 ml. of ethyl acetate. The resulting precipitate was filtered, and the filtrate washed with water (3×10 ml.) and a brine solution (2×5 ml.). The dried organic phase was concentrated to about 20 ml. and was treated with 190 mg. of p-toluenesulfonic acid monohydrate and 2 drops of water in 5 ml. of ethyl acetate. Stirring was continued for 3-4 minutes at which time a precipitate formed. After stirring for 10 minutes the desired product is filtered and dried, 520 mg.

The product is indistinguishable from that obtained in Example 13.

EXAMPLE 16

Chloromethyl 6-(alpha-1-methoxycarbonylpropen-2-ylaminophenylacetamido)penicillanate To 400 ml. of bromochloromethane at −10° C. was added 20 g. of tetrabutylammonium 6-(alpha-1-methoxycarbonylpropen-2-ylaminophenylacetamido)penicillanate and the reaction mixture allowed to stir at −10° to 0° C. for 6 hours and allowed to stand at room temperature overnight. The mixture was concentrated in vacuo and the residue chromatographed on 500 g. of silica gel using ethyl acetate-hexane (80:20, v:v) of the eluent. The fractions containing the product were combined and concentrated to a foam, 14.4 g.

The product was essentially the same as that prepared in Example 15A.

Starting with bromochloromethane in place of iodochloromethane in Examples 1 through 5 gives the corresponding chloromethyl esters.

I claim:

1. A process for the preparation of a compound selected from those of the formula

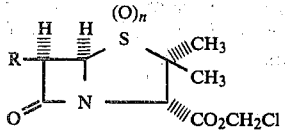

wherein n is an integer of 0 or 2, R is selected from the group consisting of (a) hydrogen, (b) 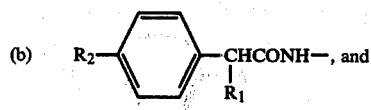

(c) 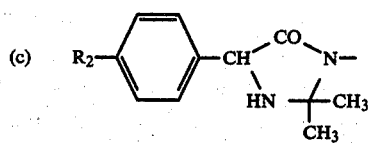

wherein $R_2$ is selected from the group consisting of hydrogen and hydroxy and $R_1$ is selected from the group consisting of azido, amino, carbobenzyloxyamino and 1-methoxycarbonylpropen-2-ylamino, which comprises contacting one mole of a compound of the formula

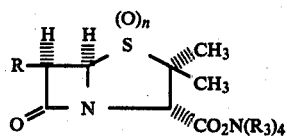

wherein $R_3$ is alkyl having from one to four carbon atoms, with at least one mole of a solvent selected from the group consisting of bromochloromethane and iodochloromethane at from about −20° C. to about 25° C. with the proviso that when n is 2, R is hydrogen.

2. The process of claim 1, wherein the reaction is conducted in the presence of excess bromochloromethane.

3. The process of claim 2, wherein R is hydrogen, $R_3$ is n-butyl and n is 2.

4. The process of claim 2, wherein R is

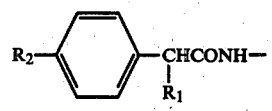

5. The process of claim 4, wherein $R_2$ is hydrogen, n is 0 and $R_3$ is n-butyl.

6. The process of claim 5, wherein $R_1$ is azido.

7. The process of claim 5, wherein $R_1$ is amino.

8. The process of claim 5, wherein $R_1$ is 1-methoxycarbonylpropen-2-ylamino.

9. A process for the preparation of a compound selected from those of the formula

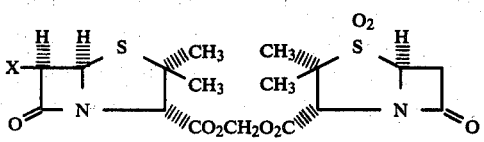

wherein X is selected from the group consisting of (a) 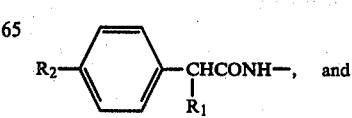

-continued

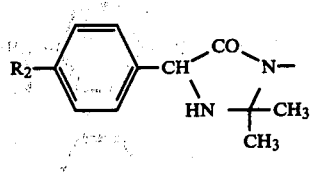 (b)

wherein R₁ is selected from the group consisting of azido, amino, carbobenzyloxyamino and 1-methylcarbonylpropen-2-ylamino and R₂ is selected from the group consisting of hydrogen and hydroxy, which comprises contacting one mole of a compound selected from those of the formula

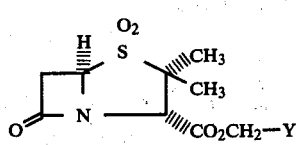

wherein Y is selected from the group consisting of chloro, bromo and iodo, with at least one mole of a compound selected from those of the formula

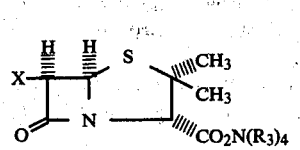

wherein R₃ is alkyl having from one to four carbon atoms in a reaction-inert solvent at ambient temperatures.

10. The process of claim 9, wherein the reaction-inert solvent is selected from the group consisting of acetone and dimethylformamide.

11. The process of claim 10, wherein X is

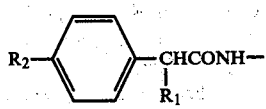

wherein R₂ is hydrogen, Y is iodo and R₃ is n-butyl.

12. The process of claim 11, wherein R₁ is azido.
13. The process of claim 11, wherein R₁ is amino.
14. The process of claim 11, wherein R₁ is methoxycarbonylpropen-2-ylamino.

15. A process for the preparation of a compound selected from those of the formula

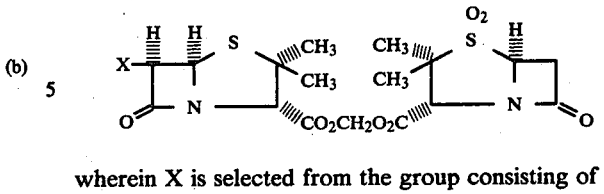

wherein X is selected from the group consisting of

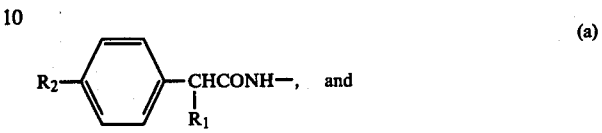 (a)

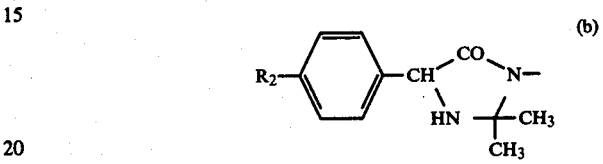 (b)

wherein R₁ is selected from the group consisting of azido, amino, carbobenzyloxyamino, and 1-methoxycarbonylpropen-2-ylamino and R₂ is selected from the group consisting of hydrogen and hydroxy, which comprises contacting one mole of a compound selected from those of the formula

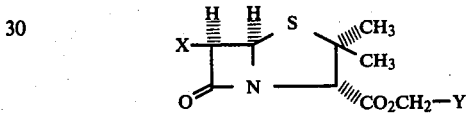

with at least one mole of a compound selected from those of the formula

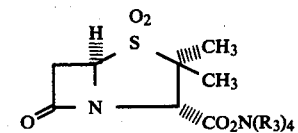

wherein R₃ is alkyl having from one to four carbon atoms and Y is selected from the group consisting of chloro, bromo and iodo, in a reaction-inert solvent at from about 0° to about 60° C.

16. The process of claim 15, wherein the reaction-inert solvent is selected from the group consisting of acetone and dimethylformamide.

17. The process of claim 16, wherein X is

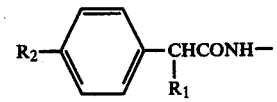

wherein R₂ is hydrogen, R₃ is n-butyl and Y is chloro.

18. The process of claim 17, wherein R₁ is azido.
19. The process of claim 17, wherein R₁ is amino.
20. The process of claim 17, wherein R₁ is 1-methoxycarbonylpropen-2-ylamino.

* * * * *